(12) United States Patent
Fruchey et al.

(10) Patent No.: US 9,290,430 B2
(45) Date of Patent: Mar. 22, 2016

(54) ACRYLIC ACID FROM LACTIDE AND PROCESS

(71) Applicant: SGA Polymers, LLC, South Charleston, WV (US)

(72) Inventors: Olan S. Fruchey, Hurricane, WV (US); Thomas A. Malisezewski, Charleston, WV (US); John E. Sawyer, Charleston, WV (US)

(73) Assignee: SGA Polymers, LLC, South Charleston, WV (US)

( * ) Notice: Subject to any disclaimer, the term of this patent is extended or adjusted under 35 U.S.C. 154(b) by 0 days.

(21) Appl. No.: 14/690,620

(22) Filed: Apr. 20, 2015

(65) Prior Publication Data

US 2015/0232404 A1 Aug. 20, 2015

Related U.S. Application Data

(62) Division of application No. 13/226,286, filed on Sep. 6, 2011, now Pat. No. 9,012,686.

(51) Int. Cl.
| | |
|---|---|
| *C07C 67/10* | (2006.01) |
| *C07C 67/08* | (2006.01) |
| *C07C 51/43* | (2006.01) |
| *C07C 51/09* | (2006.01) |
| *B01J 35/02* | (2006.01) |

(52) U.S. Cl.
CPC .................. *C07C 51/09* (2013.01); *B01J 35/02* (2013.01); *C07C 51/43* (2013.01); *C07C 67/08* (2013.01); *C07C 67/10* (2013.01)

(58) Field of Classification Search
CPC ........ C07C 67/10; C07C 67/08; C07C 51/43; C07C 51/09
USPC ............................................ 562/598; 560/234
See application file for complete search history.

(56) References Cited

U.S. PATENT DOCUMENTS

| | | | |
|---|---|---|---|
| 2,408,177 | A | 9/1946 | Ratchford et al. |
| 2,469,701 | A | 5/1949 | Redmon |
| 2,859,240 | A | 11/1958 | Holmen |
| 3,948,856 | A | 4/1976 | Stackman |
| 4,729,978 | A | 3/1988 | Sawicki |
| 4,786,756 | A | 11/1988 | Paparizos et al. |
| 5,068,399 | A | 11/1991 | Naito et al. |
| 5,252,473 | A | 10/1993 | Walkup et al. |
| 6,992,209 | B2 | 1/2006 | Lilga et al. |
| 7,538,247 | B2 | 5/2009 | Craciun et al. |
| 2004/0110974 | A1 | 6/2004 | Lilga et al. |
| 2005/0222458 | A1 | 10/2005 | Craciun et al. |

OTHER PUBLICATIONS

C.H. Holten, "Acylated Lactic Acid," Verlag Chemie, Weinheim, Chapter XV, p. 343-358 (1971).
R. Burns, D.T. Jones and P.D. Ritchie, "Studies in Pyrolysis. Part I. The Pyrolysis of Derivatives of a-Acetoxypropionic Acid and Related Subsances." J. Chemical Society, p. 400 (1935).
W.P. Ratchford and C.H. Fisher, "Methyl Acrylate by Pyrolysis of Methyl Acetoxypropionate", Industrial and Engineering Chemistry, vol. 37, p. 382 (1945).
L.T. Smith, C.H. Fisher, W.P. Ratchford and M.L. Fein, "Pyrolysis of Lactic Acid Derivatives. Conversion of Methyl a-Acetoxypropionate to Methyl Acrylate", Industrial and Engineering Chemistry, vol. 34, p. 473 (1942).
M.L. Fein and C.H. Fisher, "Acetylation of Alkyl Lactates. Methyl and Ethyl Alpha-Acetoxypropionates", Industrial and Engineering Chemistry, vol. 36, p. 235 (1944).
E.M. Filachione and C.H. Fisher, "Preparation from Lactic Acid, Acetic Acid and Methanol", Industrial and Engineering Chemistry, vol. 36, p. 472 (1944).
C.H. Fisher, W.P. Ratchford and L.T. Smith, M.L. Fein, "Methyl Acrylate Production. By Pyrolysis of Methyl Acetoxypropionate", Industrial and Engineering Chemistry, vol. 36 p. 229 (1944).
W.P. Ratchford, C.E. Rehberg and C.H. Fisher, J., "Preparation of Acrylic and Methacrylic Acids by Pyrolysis of their Alkyl Esters", American Chemical Society, vol. 66, p. 1864 (1944).
S. Varadarajan and D.J. Miller, "Catalytic Upgrading of Fermentation-Derived Organic Acids", Biotechnology Progress, vol. 15, p. 845 (1999).
H. R. Snyder, F. W. Wyman, "Synthesis and Reactions of Some Substituted Naphthaleneboronic Acids", J. Am. Chem. Soc., 1948, vol. 70, pp. 234-237.

*Primary Examiner* — Yevegeny Valenrod
(74) *Attorney, Agent, or Firm* — Dinsmore & Shohl LLP; Monika L. Jaensson, Esq.

(57) ABSTRACT

Technical grade acrylic acid derived from renewable resources utilizing a homogeneous nickel catalyst system by a process including reacting lactide with acetic acid to form 2-acetoxypropionic acid in the presence of a homogeneous nickel catalyst, pyrolyzing, with or without a catalyst, the 2-acetoxypropionic acid to acrylic acid and acetic acid, condensing and collecting the pyrolysis products in the presence of polymerization inhibitor(s) and purifying the acrylic acid by distillation in the presence of polymerization inhibitor(s). Acrylic acid and methyl acrylate are produced from methyl 2-acetoxypropionate which comes from fermentation derived lactic acid. The disclosed process will produce a "green" (i.e. renewable resources derived) acrylic acid and methyl acrylate ester.

19 Claims, 4 Drawing Sheets

ACRYLIC ACID FROM LACTIDE AND PROCESS

BACKGROUND OF THE INVENTION

The present invention is generally directed toward a process to create acrylic acid and methyl acrylate esters. More specifically, the present invention is directed toward a process to create technical grade acrylic acid or/and methyl acrylate ester from renewable resources.

For purposes of this invention, the term green technical grade acrylic acid or green acrylic acid refers to technical grade acrylic acid derived from renewable resources.

The acrylic acid market is measured by the production of crude acrylic acid. Crude acrylic acid (also known as technical grade acrylic acid) is not an item of commerce. However, it is either further purified into glacial acrylic acid or converted into Acrylate esters. The market is equally split between glacial and ester production (i.e. 50% of the crude goes to glacial and 50% goes to esters). The worldwide capacity for crude acrylic acid has been estimated at over 9 billion pounds per year.

All current production of crude acrylic acid is via a two stage air oxidation of propylene. In the first stage propylene is oxidized to acrolein using an expensive Bi/Mo based mixed metal oxide catalyst. In the second stage the acrolein is oxidized to acrylic acid using an expensive Bi/V based mixed metal oxide catalyst. Both oxidation steps are conducted at high temperature (320° C. and 280° C., respectively) in very expensive shell and tube reactors using molten salt heat exchange fluids.

The hot gases exiting the second reactor are rapidly cooled and the non-condensibles are separated from the condensed aqueous acrylic acid solution in the absorber. The concentration of the acrylic acid in this aqueous solution depends on the technology employed. One technology uses steam injection into the reactors to control flammability and the other uses recycle gas injection instead of steam. Steam injection can lead to an aqueous acrylic acid solution as low as ~20% while recycle gas injection can produce an aqueous acrylic acid as high as 70% leaving the absorber.

This aqueous acrylic acid is then subjected to a complicated purification system consisting of several towers to produce crude acrylic acid (technical grade). In the first tower water is removed. If steam was used as the diluent in the reactors the water is removed via extraction and azeotropic distillation is used if recycle gas was employed. In both cases the dewatered acrylic acid is then subjected to multiple vacuum distillations to remove both light and heavy by-products. The final product from these distillation steps is technical grade acrylic acid (>99% purity).

The capital cost for a crude acrylic acid unit is very high. Furthermore, the high raw material cost of propylene make it vulnerable to a new technology for some of the future Acrylic acid production units.

Currently, there is no commercially viable micro-organism which can directly produce acrylic acid via fermentation. However, there are known micro-organisms which can produce specific hydroxypropionic acids (acrylic acid precursors) via glucose fermentation. There are two configurational isomers of hydroxypropionic acid. The alpha isomer is commonly known as lactic acid and the beta isomer is better known a 3-hydroxypropionic acid (3HPA). Lactic acid has been produced on a commercial scale via fermentation for over one hundred years while 3HPA is not yet commercially available.

Both isomers undergo acid catalyzed dehydration yielding acrylic acid, see Chemical Reaction 1 as illustrated in FIG. 1.

However, the two isomers yield different amounts of acrylic acid. The beta isomer (3HPA) dehydrates in near quantitative yields while the alpha isomer (lactic acid) only realizes ~55% yield. These dehydration efficiencies are essentially the same for both the free acids and the corresponding lactate esters. The reason for this difference in selectivity to acrylic acid is most likely related to the location of the intermediate carbocation. Lactic acid proceeds through a carbocation alpha to the carbonyl (which can readily undergo decomposition) and 3HPA proceeds through a carbocation beta to the carbonyl (i.e. the positive charge is removed from the carbonyl and can only readily eliminate a proton forming acrylic acid).

While the dehydration of lactic acid to acrylic acid has been studied for over 50 years, the yield remains poor. This poor dehydration efficiency is also observed for lactate esters. However, it has been shown that the acetylated product of lactic acid (2-acetoxypropionic acid) readily undergoes pyrolysis to acrylic acid in ~95% yields, see Chemical Reaction 2 as illustrated in FIG. 2. High yields have also been reported for the pyrolysis of methyl 2-acetoxypropionate.

This pyrolysis reaction is a cyclic elimination of acetic acid and goes in high yields because it does not proceed through the carbocation intermediate associated with the dehydration of lactic acid. Obviously lactic acid could be converted into this acetoxy derivative and then pyrolyzed to produce acrylic acid in high yields. The problem with this route is that the acetoxy derivative would be typically made by reaction of lactic acid with either acetic anhydride or ketene. The recovered acetic acid could be converted back to anhydride or ketene using a ketene furnace, but a ketene furnace is very expensive. Furthermore, the lactic acid is only available as an aqueous solution so excess ketene or anhydride would be consumed by the water present in the aqueous lactic acid further decreasing the economics of this route. To utilize this route via the acetoxy derivative one must be able to prepare it directly from acetic acid.

Thus, there is a need for a more effective and efficient process to create acrylic acid and methyl acrylate ester.

BRIEF SUMMARY OF THE INVENTION

The present invention satisfies the needs discussed above. The present invention is generally directed toward a process to create acrylic acid. More specifically, the present invention is directed toward a process to create technical grade acrylic acid from renewable resources.

It is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein are for the purpose of description and not of limitation.

One aspect of the present invention discloses the use of a nickel catalyst system with lactide (or other oligomers of lactic acid) and methyl acetate to achieve high conversions of 2-acetoxypropionate. After the contents are subjected to pyrolyzation, a mixture of methyl acrylate and acetic acid is obtained. This mixture can be transesterified to an equilibrium mixture of acrylic acid, acetic acid, methy acetate and methy acrylate. After distillation, the resulting semi-purified acrylic acid would be a technical grade acrylic acid, and the methyl acetate returns to the first reaction. The methyl acrylate and acetic acid can be recycled to the transesterification of some of the methyl acrylate can be taken as a product.

Upon reading the above description, various alternative embodiments will become obvious to those skilled in the art. These embodiments are to be considered within the scope and spirit of the subject invention, which is only to be limited by the claims which follow and their equivalents.

DESCRIPTION OF THE INVENTION

The present invention satisfies the needs discussed above. The present invention is generally directed toward a process to create acrylic acid. More specifically, the present invention is directed toward a process to create technical grade acrylic acid from renewable resources.

Figure 1:
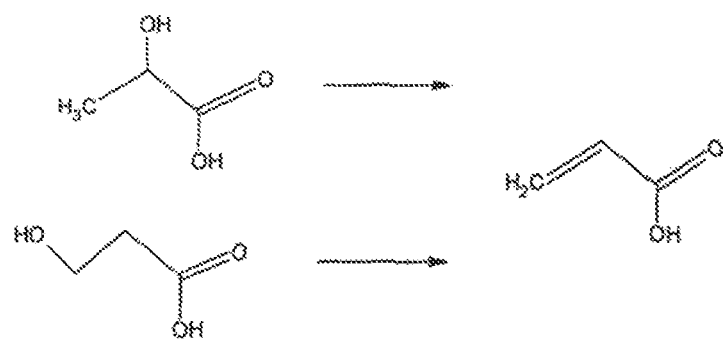
FIG. 1 is a chemical representation of an isomer undergoing acid catalyzed dehydration yielding acrylic acid.
Figure 2:
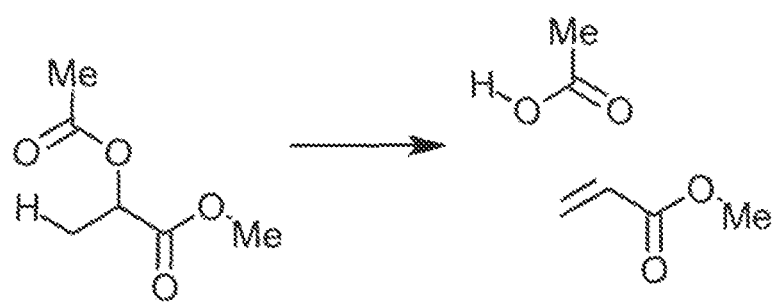
FIG. 2 is a chemical representation of an acetylated product of lactic acid (2-acetoxypropionic acid) undergoing pyrolysis to acrylic acid.
Figure 3:
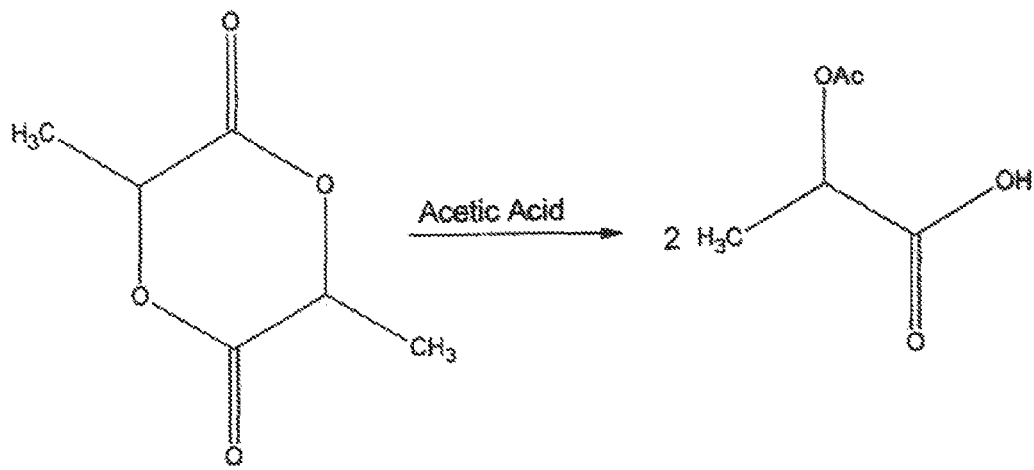
FIG. 3 is a chemical representation of the opening of a lactide by reaction with acetic acid.

Green acrylic acid and acrylate products are prepared from fermentation derived lactic acid. Lactide (ananhydrous solid) is currently produced commercially from aqueous lactic acid and used as the monomer for the production of polylactic acid. Accordingly, it is possible to open the lactide by reaction with acetic acid. See Chemical Reaction 3 as illustrated as FIG. 3.

Figure 4:
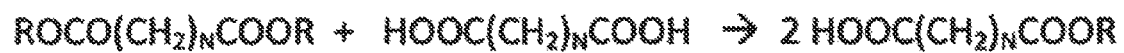
FIG. 4 is a chemical representation of the equilibration of a diacid with a diester forming the monoester.

This reaction is analogous to the known equilibration of a diacid with a diester forming the monoester, see Chemical Reaction 4 as illustrated as FIG. 4.

Figure 5:
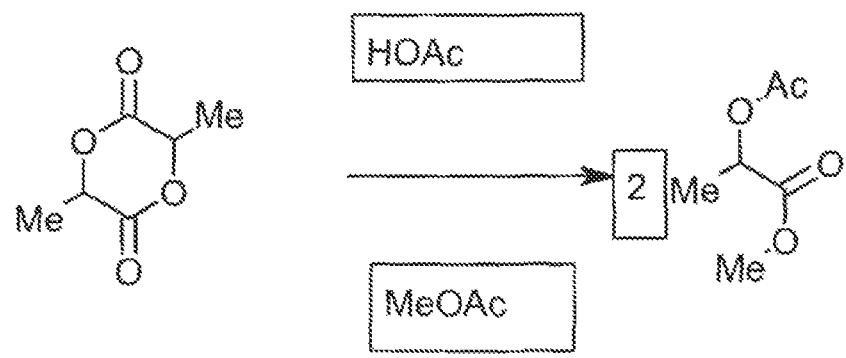
FIG. 5 is a chemical representation of a catalyst converting lactide and methyl acetate into methyl 2-acetoxypropionate.

However, the simple equilibrium reaction suffer from low conversions. A catalyst would need to be utilized to force the reaction to completion. The present invention discloses the use of a catalyst system prepared by placing nickel acetate and nickel nitrate in acetic acid which should achieve high conversions of lactide to 2-acetoxypropionic acid at high temperature (~250° C.). This nickel system is a good catalyst for the acid interchange reaction shown in Chemical Reaction 3. The same catalyst has also been shown to convert lactide and methyl acetate (in the presence of a small amount of acetic acid) into methyl 2-acetoxypropionate, see Chemical Reaction 5 as illustrated in FIG. 5.

This same reaction can be applied to any relatively anhydrous oligomer or polymer of lactic acid. In other words, lactide (the cyclic dimer of lactic acid) is only one of several possible feeds for the envisioned process.

The catalyst for this reaction can be a mixture of any transition metal salt of a strong inorganic acid and a transition metal salt of an aliphatic carboxylic acid. Examples of preferred transition metals are iron, cobalt, nickel and manganese. Examples of preferred inorganic acid salts are nitrate, chloride or perchlorate salts. The preferred carboxylic acid salt is acetate but could be any carboxylic acid salt. In other words, the catalyst for this reaction is not limited to a mixture of nickel nitrate and nickel acetate.

Figure 6:
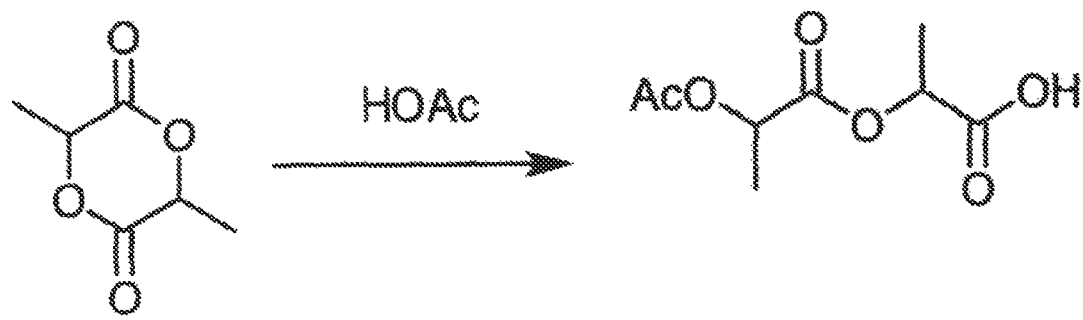
FIG. 6 is a chemical representation of a catalyst opening a lactide to the acetoxy dimer of lactic acid.

In one embodiment, at a low temperature (~115° C.) the catalyst opens the lactide to the acetoxy dimer of lactic acid, see Chemical Reaction 6 as illustrated in FIG. 6. In this case only one acid interchange reaction is occurring compared to the two acid interchange reactions that occur in Chemical Reaction 3. This acetoxy dimer of lactic acid can also under the same pyrolysis reaction as acetoxypropionic acid but in this case the reaction will yield one molecule of acetic acid and two molecules of acrylic acid.

The acrylic acid unit of the present invention consists of a reaction step in which lactide is reacted with acetic acid (both a reactant and a solvent for the reaction) in the presence of the nickel catalyst forming either 2-acetoxypropionic acid or the acetoxy dimer. The 2-acetoxypropionic acid (or acetoxy dimer) would then be pyrolyzed to acrylic acid and acetic acid. This pyrolysis can be done either with or without a catalyst. One possible catalyst for the pyrolysis step would be calcium sulfate. Additional catalysts include zeolites such as USY, mordenite, H-ZSM-5, an X zeolite, beta zeolite, or Sn-beta zeolite; mesoporous molecular sieves such as MCM-41; naturally occurring acidic clays such as montmorillonite or kaolinite; an acidic metal oxide such as alumina, tin (IV) oxide, molybdenum oxide; acidic non-metal oxides such as silica or phosphorous pentoxide; an acidic doped metal oxide such as sulfated zirconia, tungstated zirconia, sulfonated silica, tungstated tin oxide, W—Nb mixed-oxides; a Lewis acid such as $FeCl_3$, $AlCl_3$, $ScCl_3$, or other transition metal salt of a mineral acid; hetero-poly acids such as tungstosilicic acid, molybdosilicic acid, tungstophosphoric acid, and molybdophosphoric acid; or a support doped with one of the foregoing classes of acidic catalysts and combinations and mixtures thereof. All of the foregoing catalysts may be supported on standard catalytic supports for catalysts such as a monolithic structure (as is commonly used in the automotive catalyst industry to support the exhaust catalysts), beaded or pelleted supports, and other structured supports like structured packings. The catalytic material may be used to make the entire support structure, or the catalyst may be added to the surface of an inert support structure by the standard techniques of washcoating or solution impregnation. Suitable inert supports for the monolithic structure or pellets or beads include cordierite, alumina, titania, zirconia, metals such as steel, silica, silicon carbide, boron nitride, silicon nitride, and other inert heat resistant materials.

The pyrolysis products would then be condensed and collected in a receiver. The contents of the receiver would be fed to a distillation tower where acetic acid and the crude acrylic acid would be separated. The crude acrylic acid would be sent to two towers for purification. The first tower would remove light ends and the second tower Would remove heavy ends. The final product would be the overhead of the second tower. The recovered acetic acid would be recycled to the lactide reaction step.

The distillation steps involving acrylic acid would be done in the presence of polymerization inhibitors (e.g. phenothiazine, hydroquinone, p-methoxyphenol, 4-hydroxy TEMPO, etc.). The semi-purified acrylic acid from the distillation steps would be a technical grade acrylic acid which could be further purified to glacial acrylic acid by melt crystallization or reacted with a C-1 to C-8 alcohol to produce an acrylate ester. The glacial acrylic acid product would be stabilized by the addition of 200 ppm of MeHQ for commercial sales and the purified acrylate ester would be stabilized with 15 ppm of MeHQ.

Figure 7:
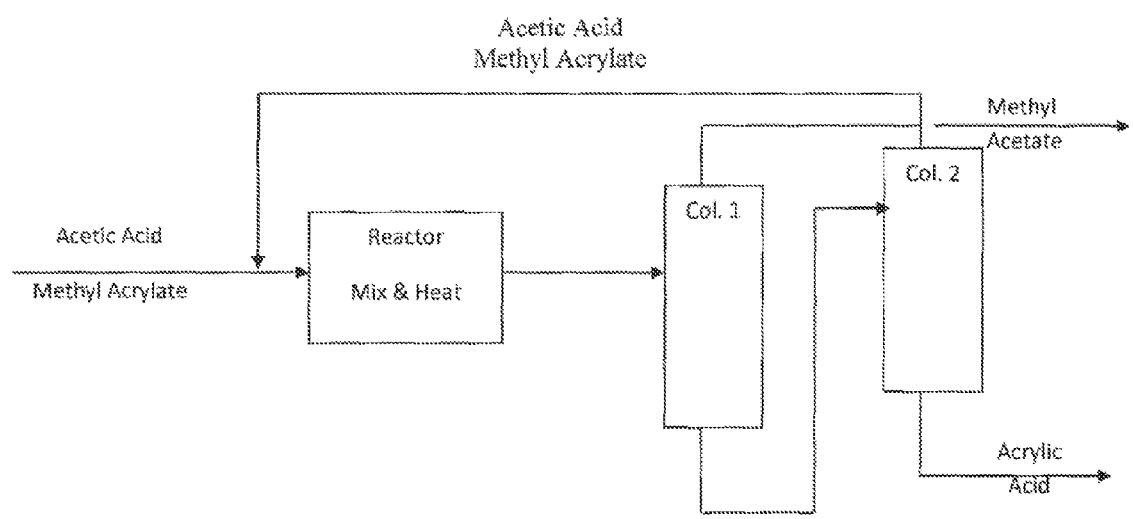
FIG. 7 is a flow diagram of an embodiment of the transesterification process of the present invention.

As illustrated in FIG. 7, another embodiment of the present invention involves a single transesterification reaction with minimal equipment. An oligomer of lactic acid is first converted into methyl 2-acetoxypropionate by reaction with methyl acetate and then pyrolyzed to a mixture of acetic acid and methyl acrylate. The effluent from this payrolysis reactor will be sent to a transesterification Reactor, with a residence time of 30 minutes to 2 hours. The transesterification Reactor will be warm (~80° C.) and will have a tranesterification catalyst. The transesterification catalyst can either be a liquid or solid. Possible liquid catalysts would be mineral acids such as sulfuric acid or phosphoric acid. Other possible liquid catalyst would be organic sulfonic acids such as methane sulfonic acid or benzene sulfonic acid. Possible solid catalyst would be polymeric sulfonic acids like Amberlyst 30 or Marathon C.

The Reactor is fed methyl acrylate and acetic acid. Transesterification occurs in this reactor. One possible version of this reactor is a fixed bed reactor where the tubes are filled with Amberlyst 30 resin. Given enough time (about 30 minutes to 2 hours, depending temperature and catalyst) the reaction will achieve an equilibrium distribution.

This transesterification reaction leads to a simplification of acrylic acid production by converting the methyl acrylate to the desired acrylic acid which is now ready for further refining and transesterifizing acetic acid to regenerate methyl acetate for use in the preparation of methyl 2-acetoxypropionate. This allows for methyl acetate to be recovered without azeotropes or other close boiling materials. Thus, the transesterification is accomplished without the complications of water.

The methyl acetate would be recovered as the overhead stream of the first distillation tower after the transesterification reaction. If desired the overhead could be a mixture of methyl acetate and methyl acrylate which could then be separated in a subsequent distillation step. In other words the methyl acetate is recycled to the process and methyl acrylate is recovered for further refining and sales. The acrylic acid would be recovered for further purification as the bottom stream of the second distillation column. The overhead could be either pure acetic acid or a mixture of acetic acid and methyl acrylate that would be sent back to the transesterification reactor for recycle. In other words the present invention would allow the production of acrylic acid alone in one embodiment or both acrylic acid and methyl acrylate in another embodiment. This transesterification reaction could also be performed via reactive distillation. The mixture of methyl acrylate and acetice acid along with a liquid catalyst would be fed to the middle section of a distillation tower while methyl acetate would be taken as the distillate stream and acrylic acid as the residue stream from the tower. The liquid catalyst would be those previously mentioned. Alternatively, a solid acid catalyst could be incorporated in the tower packing.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

The invention is demonstrated by but not limited by the following examples:

Example 1

A 250 mL round bottom flask was charged with 7.2 g of lactide, 60 g of acetic acid, 0.2 g nickel acetate, 0.2 g of nickel nitrate and 0.1 g of phenothiazine. The contents were refluxed for 6 hrs and then cooled to room temperature and discharged. GC analysis indicated that the lactide had been converted into the acetoxy dimer of lactic acid which is also called 2-(2'-acetoxypropanoyloxy)propanoic acid.

Example 2

A 300 mL Parr autoclave was charged with 7.2 g of lactide, 100 g of acetic acid, 0.5 g of nickel acetate, 0.5 g of nickel nitrate and 0.1 g of phenothiazine. The contents of the autoclave were heated and stirred at 250° C. and 300 psig for 4 hrs. The contents were then cooled to room temperature and discharged from the autoclave. GC analysis revealed that the lactide had been converted into 2-acetoxypropionic acid.

Example 3

A 300 mL Parr autoclave was charged with 7.2 g of lactide, 94 g of methyl acetate, 6 g of acetic acid, 0.5 g of nickel acetate, 0.5 g of nickel nitrate and 0.1 g of phenothiazine. The contents of the autoclave were heated and stirred at 225° C. and 500 psig for 4 hrs. The contents were then cooled to room temperature and discharged from the autoclave. GC analysis revealed that the lactide had been mostly converted into methyl 2-acetoxypropionate along with a small amount of 2-acetoxypropionic acid.

Example 4

A 250 mL round bottom flask was charged with 43 g methyl acrylate, 30 g acetic acid, 5 g Purolite PD206 sulfonic acid resin, 0.03 g of 4-hydroxy TEMPO and 0.01 g nitrosobenzene. The flask was fitted with a reflux condenser, a heating mantel and a magnetic stirrer. The contents were held at ~85° C. for 6 hrs. At the end of the 6 hrs, GC analysis revealed that the flask contained; 36.4% methyl acrylate, 25.4% acetic acid, 17.5% methyl acetate and 19.3% acrylic acid.

The invention claimed is:

1. A process for the production of acrylic acid which comprises the following steps:
    a. reacting methyl acetate with a lactic acid oligomer to produce methyl 2-acetoxypropionate in the presence of a catalyst and acetic acid;
    b. pyrolyzing methyl 2-acetoxypropionate to methyl acrylate and acetic acid;
    c. transesterifying in a reactor the methyl acrylate and acetic acid to a mixture of methyl acrylate, acetic acid, methyl acetate and acrylic acid with a catalyst;
    d. separating the methyl acetate for recycle to the methyl 2-acetoxypropionate reactor;
    e. separating the acrylic acid for further refining; and
    f. separating the mixture of methyl acrylate and acetic acid for recycle to the transesterification reactor.

2. The process for the production of acrylic acid of claim 1, wherein the catalyst in step A is a mixture of the acetate and nitrate salts of either nickel, cobalt, iron or manganese.

3. The process for the production of acrylic acid of claim 1 wherein the catalyst set out in step C is a mineral acid.

4. The process for the production of acrylic acid of claim 1 wherein the catalyst set out in step C is a solid acid.

5. The process for the production of acrylic acid of claim 1 wherein the catalyst is a strong acid resin.

6. The process for the production of acrylic acid of claim 1 wherein the catalyst set out in step C is an organic sulfonic acid.

7. The process for the production of acrylic acid of claim 1 wherein the lactic acid oligomer is lactide.

8. The process for the production of acrylic acid of claim 1 having the further step of purifying said acrylic acid from step into glacial acrylic acid by melt crystallization.

9. The process for the production of acrylic acid of claim 1 having the further step of converting said acrylic acid into an acrylate ester by reacting said acrylic acid with a C-1 to C-8 alcohol.

10. A process for the co-production of acrylic acid and methyl acrylate which comprises the following steps:
 a) reacting methyl acetate with a lactic acid oligomer in the presence of a catalyst and acetic acid to produce methyl 2-acetoxypropionate;
 b) pyrolyzing methyl 2-acetoxypropionate to methyl acrylate and acetic acid;
 c) transesterifying in a reactor the methyl acrylate and acetic acid to a mixture of methyl acrylate, acetic acid, methyl acetate and acrylic acid with a catalyst;
 d) separating the methyl acetate for recycle to the methyl 2-acetoxypropionate reactor;
 e) separating acrylic acid for further refining;
 f) separating the methyl acrylate for further refining; and
 g) separating acetic acid for recycle to the transesterification reactor.

11. The process for the co-production of acrylic acid and methyl acrylate of claim 10 wherein the catalyst in Step A is a mixture of the acetate and nitrate salts of either nickel, cobalt, iron or manganese.

12. The process for the co-production of acrylic acid and methyl acrylate of claim 10 wherein the catalyst set out in step C is a mineral acid.

13. The process for the co-production of acrylic acid and methyl acrylate of claim 10 wherein the lactic acid oligomer is lactide.

14. The process for the co-production of acrylic acid and methyl acrylate of claim 10 wherein the catalyst of step C is a solid acid.

15. The process for the co-production of acrylic acid and methyl acrylate of claim 10 wherein the catalyst of step C is an organic sulfonic acid.

16. The process of claim 10 in which the catalyst in step (b) is
 calcium sulfate;
 a zeolite such as USY, mordenite, H-ZSM-5, an X zeolite, beta zeolite, or Sn-beta zeolite;
 mesoporous molecular sieves such as MCM-41;
 naturally occurring acidic clays such as montmorillonite or kaolinite;
 an acidic metal oxide such as alumina, tin (IV) oxide, molybdenum oxide;
 acidic non-metal oxides such as silica or phosphorous pentoxide;
 an acidic doped metal oxide such as sulfated zirconia, tungstated zirconia, sulfonated silica, tungstated tin oxide, W—Nb mixed-oxides;
 a Lewis acid such as $FeCl_3$, $AlCl_3$, $ScCl_3$, or other transition metal salt of a mineral acid;
 hetero-poly acids such as Tungstosilicic acid, Molybdosilicic acid, Tungstophosphoric acid, and Molybdophosphoric acid; or
 a support doped with one of the foregoing classes of acidic catalysts and combinations and mixtures thereof.

17. A process for the production of technical grade acrylic acid which consists of:
 a. reacting lactide with methyl acetate to form methyl 2-acetoxypropionate in the presence of a catalyst;
 b. pyrolyzing said methyl 2-acetoxypropionate to methyl acrylate and acetic acid;
 c. condensing and collecting said pyrolysis products in the presence of one or more polymerization inhibitor;
 d. transesterifying the recovered mixture to an acrylic acid containing mixture and purifying resulting said acrylic acid mixture by distillation in the presence of said one or more polymerization inhibitor.

18. The process of claim 17 wherein said catalyst is defined as being a mixture of acetate and nitrate salts of nickel, cobalt, iron or manganese.

19. The process of claim 17 wherein said pyrolyzing said methyl 2-acetoxypropionate is performed with a catalyst.

* * * * *